(12) United States Patent
Antkowiak et al.

(10) Patent No.: US 8,967,808 B2
(45) Date of Patent: Mar. 3, 2015

(54) OPHTHALMOLOGICAL MEASURING SYSTEM AND METHOD FOR CALIBRATING AND/OR ADJUSTING THE SAME

(75) Inventors: Gerard Antkowiak, Jena (DE); Martin Hacker, Jena (DE); Ingo Koschmieder, Jena (DE); Roland Bergner, Jena (DE); Ralf Ebersbach, Schmoelln (DE); Thomas Pabst, Stadtroda (DE); Eberhard Hofmann, Bollberg (DE); Michael Guentzschel, Jena (DE); Steffen Dubnack, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 112 days.

(21) Appl. No.: 13/127,692

(22) PCT Filed: Nov. 4, 2009

(86) PCT No.: PCT/EP2009/007891
§ 371 (c)(1),
(2), (4) Date: Aug. 17, 2011

(87) PCT Pub. No.: WO2010/051974
PCT Pub. Date: May 14, 2010

(65) Prior Publication Data
US 2011/0299038 A1 Dec. 8, 2011

(30) Foreign Application Priority Data

Nov. 4, 2008 (DE) .......................... 10 2008 055 755
Sep. 30, 2009 (DE) .......................... 10 2009 043 748

(51) Int. Cl.
*A61B 3/10* (2006.01)
*A61B 3/00* (2006.01)
*A61B 5/117* (2006.01)

(52) U.S. Cl.
CPC ............... *A61B 3/0016* (2013.01); *A61B 5/117* (2013.01)
USPC ........................................... 351/221; 351/205

(58) Field of Classification Search
USPC .......................... 351/205, 206, 221, 243, 216
See application file for complete search history.

(56) References Cited

U.S. PATENT DOCUMENTS

| 4,988,186 A | 1/1991 | Hill et al. |
| 5,141,302 A | 8/1992 | Arai et al. |

(Continued)

FOREIGN PATENT DOCUMENTS

| DE | 37 50 034 T2 | 12/1994 |
| DE | 195 04 465 A1 | 8/1996 |

(Continued)

*Primary Examiner* — Thomas K Pham
*Assistant Examiner* — Sharrief Broome
(74) *Attorney, Agent, or Firm* — Patterson Thuente Pedersen, P.A.

(57) ABSTRACT

An ophthalmological measuring system, for obtaining biometric data of an eye, provided with the necessary calibration and check devices for monitoring the functionality and the calibration status. The ophthalmological measuring system includes an illumination source for illuminating an eye with light and with a sensor for recording and analyzing back-scattered or reflected light components and a controller. At least one calibration and check system integrated in the ophthalmological measuring system for monitoring the functional and calibration status is provided. A device is also provided which houses the calibration and test structures and which reads off the individual physical data therefrom by an interface. The ophthalmological measuring system is in particular provided for determining biometrical data but can also be used for ophthalmological, dermatological or other devices which require calibration and/or functional checking at regular intervals.

28 Claims, 4 Drawing Sheets

(56) References Cited

U.S. PATENT DOCUMENTS

| | | | |
|---|---|---|---|
| 5,321,501 | A | 6/1994 | Swanson et al. |
| 5,474,066 | A * | 12/1995 | Grolman .................. 600/398 |
| 5,903,334 | A | 5/1999 | Sakurai et al. |
| 6,030,343 | A | 2/2000 | Chechersky et al. |
| 6,481,847 | B1 | 11/2002 | Bergner et al. |
| 6,739,721 | B2 | 5/2004 | Altmann |
| 6,802,609 | B2 | 10/2004 | Mihashi et al. |
| 7,322,699 | B2 | 1/2008 | Barth et al. |
| 7,401,921 | B2 | 7/2008 | Baker et al. |
| 7,794,082 | B2 | 9/2010 | Bergner et al. |
| 7,891,812 | B2 | 2/2011 | Larichev et al. |
| 2005/0007551 | A1 | 1/2005 | Wakil et al. |
| 2007/0291277 | A1 * | 12/2007 | Everett et al. .................. 356/497 |
| 2008/0204656 | A1 | 8/2008 | Fujita et al. |

FOREIGN PATENT DOCUMENTS

| | | |
|---|---|---|
| DE | 198 57 001 A1 | 6/2000 |
| DE | 199 36 571 B4 | 2/2001 |
| DE | 101 22 248 A1 | 12/2001 |
| DE | 10 2005 025 406 A1 | 12/2006 |
| DE | 10 2005 062 238 A1 | 7/2007 |
| DE | 20 2005 021 287 U1 | 10/2007 |
| EP | 1 714 627 A2 | 10/2006 |
| JP | 62 80603 | 4/1987 |
| WO | WO 02/11612 A1 | 2/2002 |
| WO | WO 2006/128596 A1 | 12/2006 |
| WO | WO 2007079835 A1 * | 7/2007 .............. A61B 3/10 |

* cited by examiner

OPHTHALMOLOGICAL MEASURING SYSTEM AND METHOD FOR CALIBRATING AND/OR ADJUSTING THE SAME

PRIORITY CLAIM

The present application is a National Phase entry of PCT Application No. PCT/EP2009/007891, filed Nov. 4, 2009, which claims priority from German Application No 102008055755.2, filed Nov. 4, 2008, and German Application No. 102009043748.7, filed Sep. 30, 2009, the disclosures of which are hereby incorporated by reference herein in their entirety.

FIELD OF THE INVENTION

The present invention relates to an ophthalmological measuring system for the extraction of the biometric data of an eye, which exhibits the calibration and test devices necessary for the verification of the functionality and the state of calibration. Hereby, the calibration and adjustment of such optical devices is effected with the aid of at least one such calibration or test device.

BACKGROUND

The calibration and test devices used in ophthalmological measuring systems are hereby also termed reference objects and particularly as so-called test eyes.

With certain technical and particularly medical devices, a recurring calibration and adjustment is necessary during the routine process in order to ensure the required quality, proper functioning, and safety of the devices. Thereby, the increasingly sought after enhancement of the measurement accuracy of technical devices is contradictory to the feasibility of the simple and reproducible accuracy of the calibration and test devices.

Users of ophthalmological instruments are often encouraged to attach calibration and test devices in predetermined intervals, and/or before measurements of the patient, to the instrument, measure said instrument and compare the obtained measurements with the presets. This applies particularly to devices for biometry, keratometry, topography of the eye, or also Scheimpflug cameras. Hereby, complex light structures, such as slices, rings, slits, or the like, must be projected, sometimes simultaneously, with large and/or very different angles onto the eye.

According to prior art, ophthalmological measuring systems for the determination of the biometric data of an eye as well as calibration and test devices for the verification of the functionality and the state of calibration in the form of test eyes are sufficiently known, whereby calibration and test devices in the form of scale representations or surface representations are hereby used.

In ophthalmology, the calibration and test devices in the form of test eyes are therefore measured, evaluated, and appropriately marked in advance with test standards. According to known prior art, the test eyes receive only an indicator in the form of numerical values or physical size indicator, readable by the user without technical means. Thereby, the data for the test eyes to be used are stored in some cases in the optical device. For the use of other than the stored test eyes, an appropriate adjustment of the software of the optical device is required.

In other optical devices said data are not stored. The operator of the optical device to be calibrated and/or adjusted is faced with the task of manually comparing the numerical values printed on the test eye with the measurements of the optical device during the measurement of the test eye. Empirically, this can lead to incorrect decisions in day-to-day usage due to lack of care. Said incorrect decisions inevitably result in faulty measurement results and can ultimately lead to misdiagnoses and even mistreatments. Incorrect decisions or confusions due to lack of care can, among others, also lead to significant problems in a connected discipline.

For example, DE 195 04 465 A1 describes a calibration and test device for optical eye length measurement devices, particularly for interferometric measurements. Hereby, transparent spheres with an approximate diameter of 16 mm and an approximate refractive index of 2 are utilized as calibration and test devices. As a result, the radius of curvature of the surface of the test body approximately corresponds to the cornea of the eye, so that the beam path in the measuring system, as with the measurement, runs in the natural eye. In a preferred embodiment, the test body exhibits a definedly reduced transmission in order to better adjust the transmission and/or reflectivity to the conditions in the eye. Through the change of the reflectivity of the coatings of the front and/or back of the test body and their transparency, different human eyes can be recreated.

A further calibration and test device for optical eye length measurement devices is described in DE 199 36 571 B4. It comprises two plano-convex lenses, which are arranged in the illumination beam path and aligned in opposite directions, and between which a neutral filter with a defined transmission is positioned. Herewith, a test body is provided that, despite its relatively simple design, is universally applicable for optical eye length measurement devices. For the reduction of unwanted reflections on the planar plate, the entire arrangement is used at an angle of between 10 and 20 degrees. Through the use of another gray filter or the variation of its thickness, additional test spheres can be dimensioned, which simulate various haze values due to eye cataract. Advantageously, a precise absorption can be set through a variation of the tilting in the beam path since a tilting of approximately five degrees represents a transmission correction of approximately 20-25%.

According to prior art, only solutions are known for the determination of the biometric data of an eye with ophthalmological measuring systems, wherein the necessary calibration and test devices are designed as separate optical elements and utilized at regular intervals for testing the functionality and the state of calibration.

A number of known methods and measurement devices exist for the determination of the biometric data of an eye. For example, prior to a surgical procedure for exchanging the eye lens in case of a lens opacification (cataract), it is necessary to determine various biometric parameters of the eye. In order to ensure eyesight as optimal as possible after surgery, it is necessary to determine said parameters with sufficiently great accuracy. The selection of a suitable replacement lens based on the determined measurements takes place by use of established formulas and calculation methods.

The most important parameters to be determined are, among others, axial length (distance to the retina), corneal curvature and refractive power as well as the length of the anterior chamber (distance to the eye lens). These measurements can be obtained successively with different ophthalmological instruments or with the help of specially optimized biometric measurement devices.

In addition to ultrasound measurement devices, optical measurement devices on the basis of short-coherence interferometry methods have particularly prevailed for the determination of said parameters. With these methods based on short-coherence interferometry, depth profiles or two-dimensional depth cross sections of scattering potentials, particularly of scatterings at structural transitions, are depicted. Hereby, the so-called OCDR (optical coherence domain reflectometry) method and the so-called OCT (optical coherence tomography) have prevailed as short-coherent measurement methods.

With OCDR, temporally incoherent light is used with the help of an interferometer for the acquisition of depth profiles on reflective and scattering structures, and distance measurements based thereupon. In addition, as described in U.S. Pat. No. 5,321,501, imaging is realized on the reflective and/or scattering structures with OCT by means of a beam deflection. Such systems as well as Scheimpflug camera systems, e.g., are suited for obtaining biometric data from image information, such as the dimensions of the anterior chamber of the eye, needed, e.g., for the adjustment of phakic intraocular lenses.

U.S. Pat. No. 7,322,699 B2 describes a combination device for the non-contact determination of biometric data, such as axis length, anterior chamber depth as well as corneal curvature. Based on the measurement of the required data, it is possible with the described solution to perform everything from the calculation to the selection of the intraocular lens IOL to be implanted with only one device. As a result, increased stress on the patient due to multiple placings and measurements with various devices as well as data losses or data corruptions through transfer of the measurements between various devices can be avoided.

A combination device for non-contact determination of axis length, anterior chamber depth as well as corneal curvature of the eye as well as the calculation and selection of an intraocular lens IOL to be implanted, is described in DE 198 57 001 A1. The measured variables, which are also important for the selection of an intraocular lens IOL to be implanted, must be determined particularly prior to cataract surgery but also during the follow-up of school myopia and aniseikonia determination. The determined measured variables are inserted in formulas which calculate the optical effect of the IOL. Depending on the type of device to be used, various errors may occur which influence the selection of the IOL.

Until now it has been customary in the clinical practice to measure said variables by means of at least two devices (e.g., ultrasound a-scan and automatic keratometer). Since the computation of the IOL can now take place by means of a device arrangement, data losses or data corruptions are also emitted during the transfer of the measurements from various devices to the computer which effects the computation of the IOL. The IOLMaster® from Carl Zeiss Meditec AG, based on a short-coherent method, represents an optical measurement device in accordance with the described solution principle.

Usually, an included test sphere is to be measured regularly for the calibration and/or verification of the functionality measuring functions of such devices.

Thereto, e.g., a holder with a test sphere is inserted into holes positioned next to the chin rest. The test spheres display the respective nominal values and tolerances which serve the verification of the state of calibration. The device should only be activated when the measurements provide results which correspond with the nominal values on the test sphere within the also indicated tolerances. After the completed measurement, the test spheres are to be removed and safely stored in order to avoid damage and/or contamination.

US 2007/0291277 A1 describes an ophthalmological system which comprises an optical coherence tomography system (OCT), a fundus detection system, an iris detection system, a motorized chin rest, internal test structures, and a fixation marker unit. Thereby, the internal test structures, which are essentially designed as spaced surfaces as well as crosshairs, or as horizontal and/or vertical beam structures, are provided for the verification of individual functionalities. However, said internal test structures only allow for internal functional tests and calibrations of the OCT system (optical coherent tomography) and/or for the LSLO system (line scanning laser ophthalmoscope) used for fundus detection but, particularly, they do not allow for those with regard to all optical components on the entire beam path to and from the patient's eye. Therefore, in addition to the internal test structure, US 2007/0291277 A1 still contains the description of a conventional test eye which is solely designed for calibrations and, in addition, has to be attached manually.

The document WO 2006/128596 A1 describes in this context a microkeratome for application in ophthalmology, particularly for the LASIK method. With the so-called LASIK method, the cornea of an eye is cut laterally to the optical axis, producing a corneal lid, also called flap. After the flap is folded back, the ablation of the underlying stroma of the cornea is effected. This way, the cornea can be shaped in accordance with the respective defective vision. After the completed correction, the flap is returned to its original position. Thereby, the flap attaches itself on its own and coalesces without having to be sutured. Microkeratomes are used for the incision in the cornea, which, as a rule, contain replacement components to be chosen by the operator in dependence of the pending surgery. Such replacement components are particularly the cutting head and the suction ring. Different replacement components have different effects on the execution of the surgical procedure. In the solution described here, the replacement components each exhibit an identification which describes the identifying features of the respective replacement components. The identifications can be read and utilized with a reading device. The identification data can, e.g., be directly displayed for the operator on a screen and/or used as basis for a calculation for the control of the microkeratome system. The system described hereto, barcodes are preferably provided for the identification of the replacement components. This solution described hereto implies the use of an additional reading device in the form of an appropriate barcode reader and is neither designed for the calibration and/or adjustment of a device nor suited for such tasks.

SUMMARY OF THE INVENTION

Said solutions are disadvantageous because the use of external test eyes is laborious for the user and entails a crucial source of error. Understandably, storage, attaching, measuring of the test eye as well as the reading and comparing of the calibration data is not user-friendly.

The present invention is based on the task of developing an ophthalmological measuring system, particularly for the determination of the biometric data, which does not exhibit the disadvantages noted in the prior art. Thereby, the calibration and test device shall exhibit at least one test structure and be suited for application in ophthalmological instruments with pattern projection, particularly keratometers. Thereby, the calibration and/or adjustment shall be significantly easier for the operation personnel, and the error sources known from prior art shall be eliminated.

According to the invention, the task is solved in such a way through the ophthalmological measuring system, particularly for extraction of the biometric data of an eye, according to the invention, comprising at least means for the illumination of an eye with light, and means for the detection and analysis of backscattered or reflected light portions, as well as a control unit, that for the verification of the function and the state of calibration of the measuring system, at least one calibration and test device, integrated in the ophthalmological measuring system, is provided which exhibits at least one test structure, and that one device is provided in order to incorporate the calibration and test device and change its position with regard to the means for the detection of backscattered or reflected light portions. Thereto, the calibration and test device to be used is moved into the measuring position, its individual physical data are read by the ophthalmological measuring system to be calibrated and/or adjusted, its physical properties are read by the ophthalmological measuring system to be calibrated and/or adjusted, the read physical data of the calibration and test device are compared with its measured physical properties, and findings about the state of calibration and/or adjustment as well a decision for the further utilization of the ophthalmological measuring system are derived.

Even though the present invention relates to an ophthalmological measuring system, particularly for the determination of the biometric data, the inventive solution of the integration of calibration and test devices is also suited for other ophthalmological, dermatological, or even other devices which require calibrations and/or functional tests at regular intervals. This also includes measuring systems as parts of ophthalmological therapy systems, e.g., those for photocoagulation on the retina or laser treatment for a refractive correction.

BRIEF DESCRIPTION OF THE DRAWINGS

In the following, the solution is further described by means of embodiment examples. It is shown in.

DETAILED DESCRIPTION

The ophthalmological measuring system, particularly for the determination of the biometric data of an eye, according to the invention, comprises at least means for the illumination of an eye with light, and means for the detection and analysis of backscattered or reflected light portions, as well as a control unit. Hereby, the calibration and test devices necessary for a calibration as well as the verification of the function and the state of calibration are integrated in the ophthalmological measuring system, whereby the ophthalmological measuring system exhibits at least one device for the attachment and alignment of the position of at least one calibration and test device with regard to the means for the detection of backscattered or reflected light portions.

Photodetectors or even cameras are utilized as means for the detection of backscattered or reflected light portions.

Hereby, the ophthalmological measuring system can particularly exhibit means for the simultaneous illumination of an eye with light from one or several light sources and under different, particularly large angles to the visual axis of the eye of >5°, >10° or even >15°, as is, e.g., required in ophthalmological instruments for keratometry or topography.

Preferably, the calibration and test device exhibits at least one curved surface as test structure. Hereby, possible test structures are:

Test surfaces, particularly test spheres, for the determination of the radius of curvature on the cornea and/or eye lens;

Spacing structures for the calibration of measurements of partial sections such as axis length or anterior chamber depth;

Reflectors with determined degrees of reflection (attenuators) for sensitivity determination; and Test patterns for resolution tests and lateral calibration of fundus or anterior chamber images.

The device for the attachment of at least one calibration and test device exhibits a device with which the calibration and test device is moved mechanically and/or semi- or fully automatically to the position required for the measurement. One option for semi-automatic positioning, e.g., is a manual reset of the calibration and test device in the attachment device after an electromechanically triggered folding out or extending of the calibration and test device from the attachment by means of a spring. Hereby, a positioning of the calibration and test device can be realized with a minimum of electromechanical components.

Preferably, the movement of the calibration and test device to the position required for the measurement is effected motorized and fully automatically, i.e., to a predetermined or signal optimized position near the nominal position of the patient's eye. Thereto, the ophthalmological measuring system exhibits an appropriate drive unit.

However, it is also possible that the ophthalmological measuring system exhibits means with which it is aligned mechanically and/or semi- or fully automatically with the calibration and test device, or that the ophthalmological measuring system exhibits means with which the measuring beams of the ophthalmological measuring system are redirected to and/or aligned with the fixedly arranged calibration and test device.

After the alignment, a possible relative fine positioning between the calibration and test device and the measuring head might be required, so that the measuring beam, originating from an illumination unit and after reflection or backscattering at the calibration and test device, sufficiently impinges on the measuring module.

Thereto, sensors, such as photodetectors with aperture diaphragms, can be provided in the calibration and test device or in the attachment behind the calibration and test device, and which can provide a suitable feedback signal for an automatic fine positioning, or also signals for the determination of the laser power or changes in transmission at the calibration and test device, e.g., due to contamination.

Further advantageous embodiments are such that the device for the attachment of at least one calibration and test device exhibits an interface for the identification of different calibration and test devices.

Thereby, the device for the attachment of at least one calibration and test device is designed in such a way that various calibration and test devices can be attached in order to position them semi- or fully automatically for the measuring tasks. Hereby, the used calibration and test devices do not have to be of the same type but can, e.g., be provided for different types of ophthalmological instruments and their various measuring requirements. Thereto, the device for the attachment of at least one calibration and test device is always designed identically and therefore allows for universal utilization. The various calibration and test devices can be identified via the universal interface on the device. This has the additional advantage of a cost-efficient production due to identically constructed series, lower development costs, and easier assembly and repair.

In a particularly advantageous embodiment, only one drive unit is provided for the mechanical and/or semi- or fully automatic alignment of the calibration and test device with the ophthalmological measuring system and for the positioning of a headrest and/or chin rest. Said drive unit realizes a linear movement for the positioning of the headrest and/or chin rest, and a linear and/or rotating movement for the alignment of the calibration and test device. Thereto, the device for the attachment of at least one calibration and test device is hereby arranged directly at the headrest or the measuring head. Furthermore, it is advantageous that the means for the attachment of at least one calibration and test device is designed in such a way that the calibration and test device is exchangeable.

For immobilizing the patient, most ophthalmological measuring systems utilize a headrest with a chin rest which frequently exhibit a motor-driven height adjustment. The automatic control in this embodiment comprises the use of the already present motor for the chin rest. The expansion of the travel range allows for the additional movement of a test eye. Said mechanism converts the linear movement of the chin rest into a rotation solely for the test eye. As a result, the unit comprises a motorized chin rest, an extended travel range, a mechanism for minimizing the required travel range, an option for attaching a test eye or laboratory standard to the mechanism, a control unit, some elements to ensure the correct position, and optionally, a safety device so as to not endanger patients.

Figure 1:
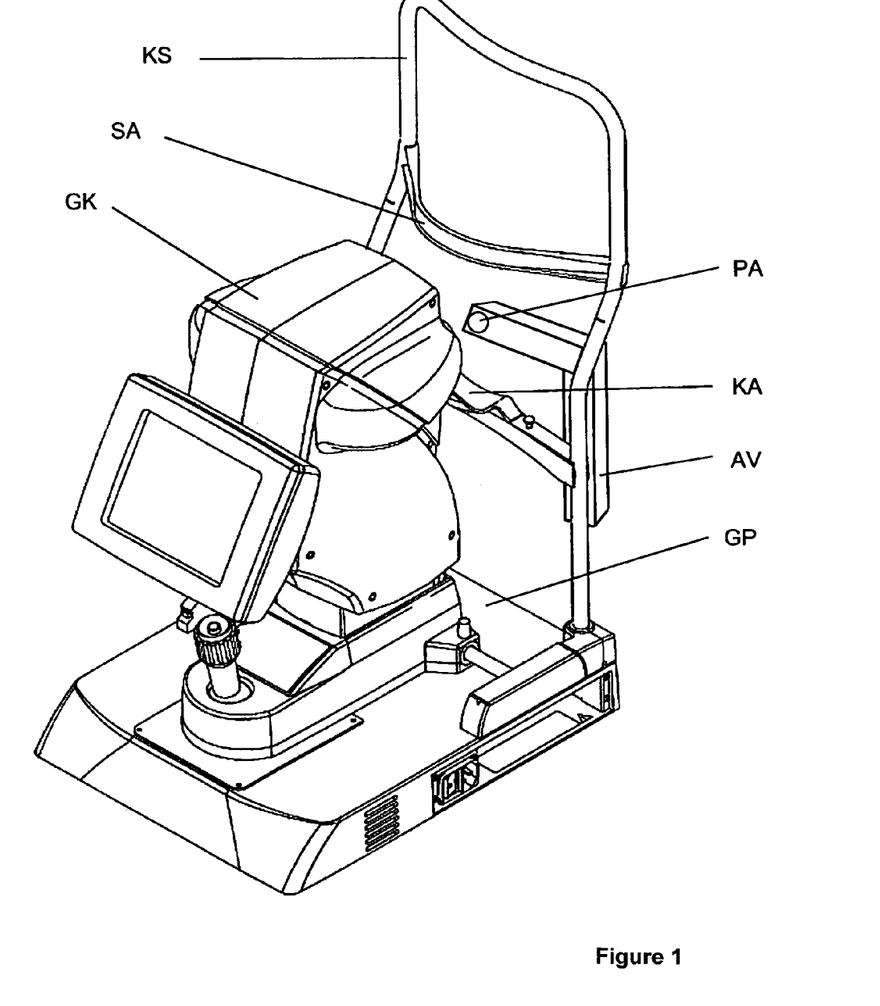
FIG. 1 is an IOLMaster® with a test eye integrated in the headrest.

In a first embodiment, FIG. 1 shows exemplary an ophthalmological measuring system in the form of an IOLMaster®, whereby the device for the attachment of at least one calibration and test device is arranged at the headrest. The IOLMaster® comprises at least one measuring head GK, adjustable in x, y, and z directions for the alignment with the eye to be examined, and which is connected via a base plate GP with a headrest KS with chin rest KA for the immobilization of the eye to be examined, as well as a control and evaluation unit (not depicted). Thereby, the required calibration and test devices are integrated in the form of a test eye PA, whereby the headrest KS exhibits a device AV for the attachment of at least one test eye PA. The device AV for the attachment of at least one test eye PA exhibits means with which the calibration and test device is moved mechanically and/or semi- or fully automatically to the position required for the measurement. Thereby, the movement can be effected, as shown in FIG. 1, through swiveling or tilting but also through a rotation or a linear extension. Preferably, the device AV thereto exhibits appropriate actuators for a fully automatic movement.

Furthermore, it is advantageous that the device AV is designed in such a way that the test eye PA is exchangeable. For a conclusive identification of the test eye PA and a conclusive assignability of the measurement data, it exhibits a serial number which can be detected electrically, optically, and/or optoelectrically. In a further advantageous embodiment, the identification of the test eye PA can be effected via its serial number by means of an RFID system (radio frequency identification).

In a further example embodiment, the calibration and test device exhibits a machine-readable identification which contains the individual physical data of the calibration and test device. In addition, the machine-readable identification can contain the tolerances necessary for the calibration and/or adjustment of the ophthalmological measuring system, and/or the information as to which calibration and test device is to be assigned to the ophthalmological measuring system. Hereby, the machine-readable identification of the calibration and test device is preferably a barcode, a data matrix code, an RFID chip, or a similar electronic memory. Thereby, it is irrelevant whether the ophthalmological measuring system is based on an interferometric measurement method or the wavefront analysis.

Figure 2:
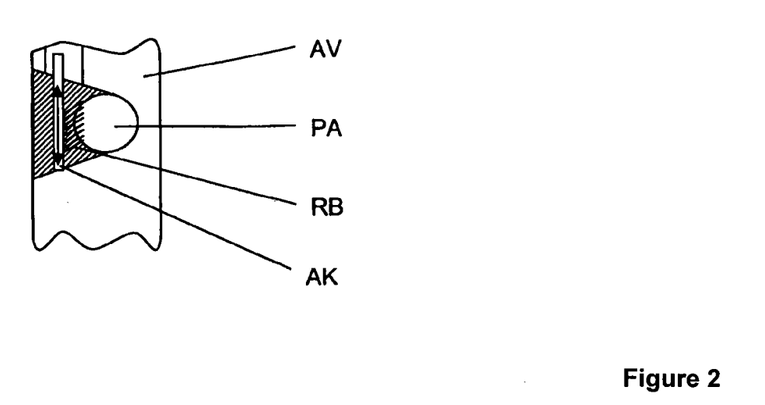
FIG. 2 depicts a device for the attachment of at least one test eye with a cover lid, and means for the cleaning of the test eye.

In order to ensure that the calibration as well as the verification of the function and the state of calibration corresponds with the respective standards, it must be ensured that the applied test eye PA is neither contaminated nor damaged. Thereto, FIG. 2 shows a further advantageous embodiment, whereby the device AV for the attachment of at least one test eye PA exhibits a cover lid AK for the protection against damage, and means for cleaning RB. In the simplest scenario, the means for cleaning RB of the test eye PA can be a brush which is arranged at the cover lid AK and wipes over and cleans the test eye PA when the lid is opened. In addition to mechanical means, pneumatic and/or acoustic means can be used for the cleaning of the test eye PA. Preferred is furthermore the use of dirt-resisting coatings or surface structures on the accessible optical surfaces of the measuring system, particularly the calibration and test device. Such coatings are described, e.g., in JP 62080603 A.

In order to avoid injuries, it must be imperatively ensured during the time of the calibration as well the verification of the functionality and the state of calibration that no patient puts his/her head against the headrest. Thereto, the ophthalmological measuring system additionally exhibits safety devices which prevent a movement of the test eye PA when a patient has already put his/her head against the headrest. For example, light barriers, or even pressure sensors, or capacitive sensors on the chin rest and/or headrest can be utilized as safety devices.

In a further example embodiment, the previously described device AV for the attachment of at least one test eye PA can be integrated with all its described advantageous embodiments in a motorized accommodation for the patient's entire head for eye examination devices or treatment devices, according to U.S. Pat. No. 7,401,921 B2. This has the advantage that the drives provided for the movement of the patient accommodation can also be utilized for a positioning of the test eye PA.

Due to the simple and compact design of the motorized patient accommodation described in U.S. Pat. No. 7,401,921 B2, it can be combined with a great number of ophthalmological devices, such as refractometers, keratometers, fundus cameras, corneal topographers, OCT-based imaging systems, wavefront sensors, laser eye surgery systems, etc.

Figure 3:
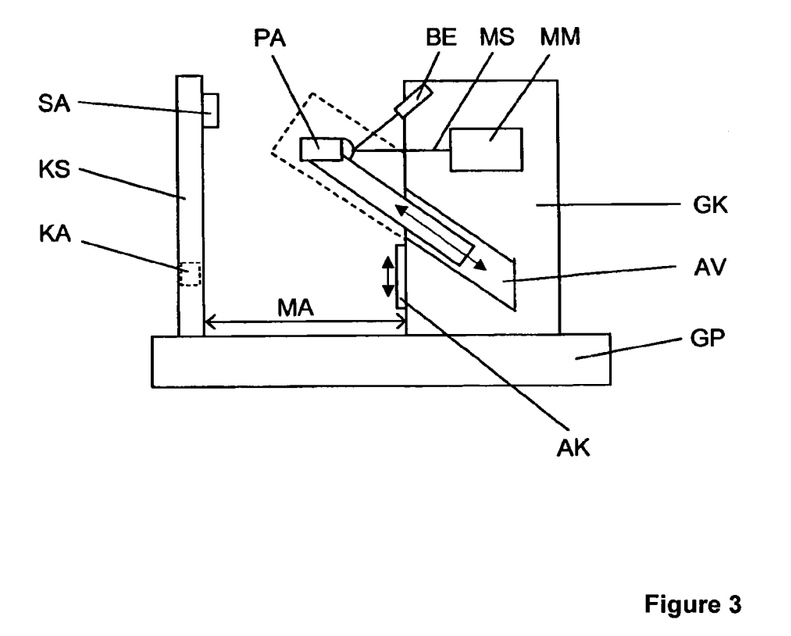
FIG. 3 depicts an ophthalmological measuring system with a test eye integrated in the measuring head of the device.

In a second realization, FIG. 3 shows exemplary an ophthalmological measuring system, whereby the device for the attachment of at least one calibration and test device is arranged directly at the measuring head of the device. The ophthalmological measuring system comprises at least one measuring head GK, adjustable in x, y, and z directions for the alignment with the eye to be examined, and which is connected via a base plate GP with a headrest KS with chin rest KA for the immobilization of the eye to be examined, as well as a control and evaluation unit (not depicted).

Thereby, the required calibration and test devices are integrated in the form of a test eye PA, whereby the measuring head GK exhibits a device AV for the attachment of at least one test eye PA. The device AV for the attachment of at least one test eye PA once again exhibits means with which the calibration and test device is moved mechanically and/or semi- or fully automatically to the position required for the measurement. Thereby, the movement is effected preferably through a linear extension but can also be realized through swiveling or tilting. Preferably, the device AV thereto exhibits appropriate actuators for a fully automatic movement.

In addition, FIG. 3 shows the test eye PA in extended position, i.e., in a measuring position for a calibration and/or verification of the functionality or the state of calibration.

After extension and/or alignment of the test eye PA, it is illuminated by an illumination unit BE. The measuring beam MS, reflected from the test structure of the test eye PA, is detected by a measuring module MM and analyzed. By means of the comparison of the determined data with the stored calibration data, it can be determined whether possible existing deviations lie within the predetermined tolerances.

In order to avoid contamination or damage of the test eye PA, the device AV for the attachment of at least one test eye PA exhibits a cover lid AK for the protection against damage, and means for cleaning (not depicted). Hereby, the means for cleaning can operate mechanically, pneumatically, and/or acoustically.

In order to avoid injuries, it must once again be imperatively ensured during the time of the calibration as well the verification of the functionality and the state of calibration that no patient puts his/her head against the headrest. Thereto, the ophthalmological measuring system additionally exhibits safety devices which prevent a movement of the test eye PA when a patient has already put his/her head against the headrest. For example, light barriers, or even pressure sensors, or capacitive sensors on the headrest KS or the chin rest KA can be utilized as safety devices.

The integration of the device AV for the attachment of at least one test eye PA in the measuring head GK is advantageous because the distance of the test eye PA is independent from the position of the headrest KS. As a result, it is possible to increase the distance between the measuring head GK and the headrest KS to a minimum distance MA prior to the extension of the test eye PA and therefore already preclude injuries to the patient. Safety devices could therefore also be dispensed with.

In a particular embodiment, the device for the attachment and change of position of the calibration and test device with regard to the means for detecting backscattered or reflected light portions is designed in such a way that, in addition to the device for the attachment of the calibration and test device, means for the movement of an additional optical element are provided in order to align the calibration and test device with regard to the means for detecting the backscattered or reflected light portions.

Hereby, a plane mirror, which is moved into the measuring beam path and deflects said measuring beam path in the direction of the calibration and test device, is, in the simplest case, used as an additional optical element. The movement is once again effected mechanically and/or semi- or fully automatically. Hereby, the calibration and test device is arranged at a distance at which the patient's eye to be examined is normally located.

Such an arrangement has the advantage that the calibration and test device can be integrated in the ophthalmological measuring system and does not have to be moved. Through a plane mirror, tilted at 45°, the measuring beam path is angled at 90°, so that the calibration and test device can, e.g., be integrated in the base of the instrument.

In this embodiment variation, the calibration and test device also exhibits at least one curved surface as test structure, and a serial number which can be detected electrically, optically, and/or optoelectrically, allowing for a clear assignment of the measurement data.

The device for the attachment of at least one calibration and test device is designed in such a way that the calibration and test device is exchangeable and preferably exhibits a cover lid for the protection of the calibration and test device and/or means for cleaning the calibration and test device.

The arrangement, according to the invention, provides an ophthalmological measuring system, particularly for the determination of the biometric data of an eye, which does not exhibit the disadvantages mentioned in prior art. The solution is particularly suited for the application in ophthalmological instruments with structure projection, particularly keratometers.

The suggested solution allows for an automatic verification of the state of calibration and functionality of ophthalmological measuring systems which until now required manual operation with a test eye. Thereby, the measuring of test eyes can be designed as standard feature to be part of the device initialization.

Furthermore, solutions are realized which do not require maintenance measures (cleaning) on the test eye, and which make confusions or errors during the reading of calibration data impossible.

The applied calibration and test device for the calibration and/or adjustment of an ophthalmological measuring system exhibits a machine-readable identification which contains the individual physical data of the calibration and test device.

Hereby, the individual physical data, which correspond to the expected values of a measurement with the calibration and test device, refer to the physical properties with regard to form, dimensions, curvatures, material and the like as well as the optical properties, e.g., with regard to refraction, reflection, transmission, and polarization, etc.

In addition, the machine-readable identification can also contain information for the positioning tasks to be realized in order to further simplify and automate the calibration and verification.

As a result, it is possible to realize the application of the device for the attachment of at least one calibration and test device and its positioning for various ophthalmological measuring systems and their different measuring requirements. This has advantages with regard to a cost-efficient production, lower development costs, as well as easier assembly and repair.

In a first advantageous embodiment, the machine-readable identification of the calibration and test device also contains the tolerances necessary for the calibration and/or adjustment of the ophthalmological measuring system, and/or the information as to which calibration and test device is to be assigned to the ophthalmological measuring system.

In a second advantageous embodiment, the machine-readable identification is arranged on the calibration and test device in the form of a barcode, a data matrix code and the like.

A barcode refers to an optoelectrically readable print which consists of parallel lines and gaps of various widths. The data from such a barcode are mechanically read with optical reading devices, such as a barcode reader, and electronically processed. A barcode is a one-dimensional code (1D code).

Contrarily, the data matrix code is a two-dimensional code (2D code), allowing for a significant increase of the information density per unit of area. Various code schemes exist for the data matrix code, whereby the code scheme "ECC 200" is the most commonly used due to its reliable readability. With this code scheme, the data are coded as a pattern of squares on a defined square or rectangular area.

In a particularly advantageous embodiment, the calibration and test device is a test eye with barcode, which is applied for the calibration and/or adjustment of an ophthalmological measuring system based on an interferometric measurement method or the wavefront analysis.

Figure 4:
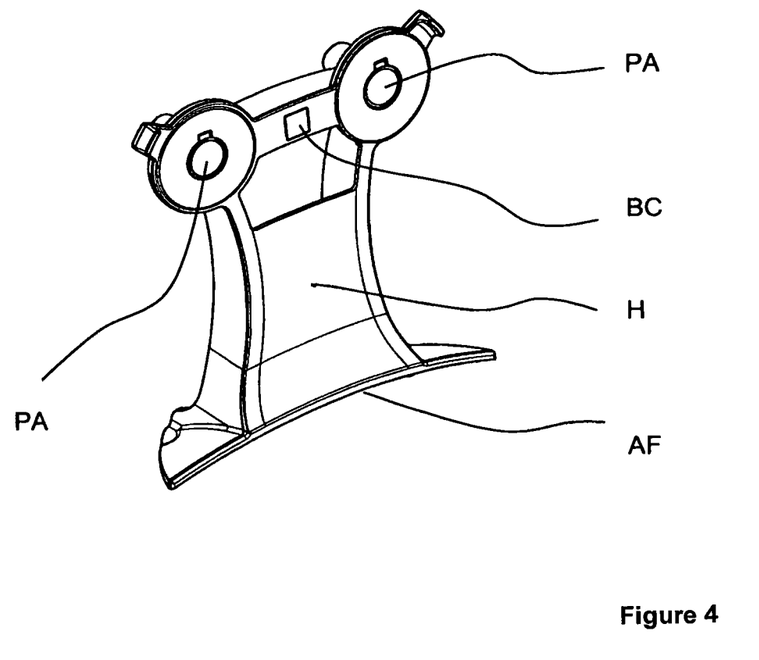
FIG. 4 depicts a calibration and test device, according to the invention, in the form of two test eyes, arranged in a holder.

Hereto, FIG. 4 shows the applied calibration and test device in the form of two test eyes PA, arranged in a holder H. Thereby, the holder H exhibits a seating surface AF for the defined arrangement of the holder H on the ophthalmological measuring system to be calibrated and/or adjusted. Hereby, the machine-readable identification in the form of a barcode BC is arranged on the holder H. Hereby, the holder H with the arranged test eyes PA is fixed mechanically by hand on the chin rest KA, and a test eye PA is moved to a position required for the measurement.

The applied calibration and test device can preferably be used for the calibration and/or adjustment of a so-called IOLMaster®. The IOLMaster® from Carl Zeiss Meditec AG is an optical measurement device based on the short-coherent method for the precise and non-contact determination of axis length, anterior chamber depth as well as corneal refractive power. Hereby, a calibration and test device in the form of a test eye PA with barcode, data matrix code, RFID chip, or a similar electronic memory is used for the calibration and/or adjustment of the IOLMaster®.

Hereby, the machine-readable identification in the form of serial numbers, barcodes, data matrix codes, an RFID chip, or a similar electronic memory can be detectable automated mechanically, electrically, optically and/or electromagnetically, so that the measurement data are clearly assignable, particularly for avoiding the necessity of an error-prone interaction with the user of the measuring system. For example, the serial number can be placed binary-coded in the form of conductor links between electrical contacts on the base. Alternatively or optionally, the calibration and test device itself can also contain the calibration data, e.g., in an electronically readable memory.

Figure 5:
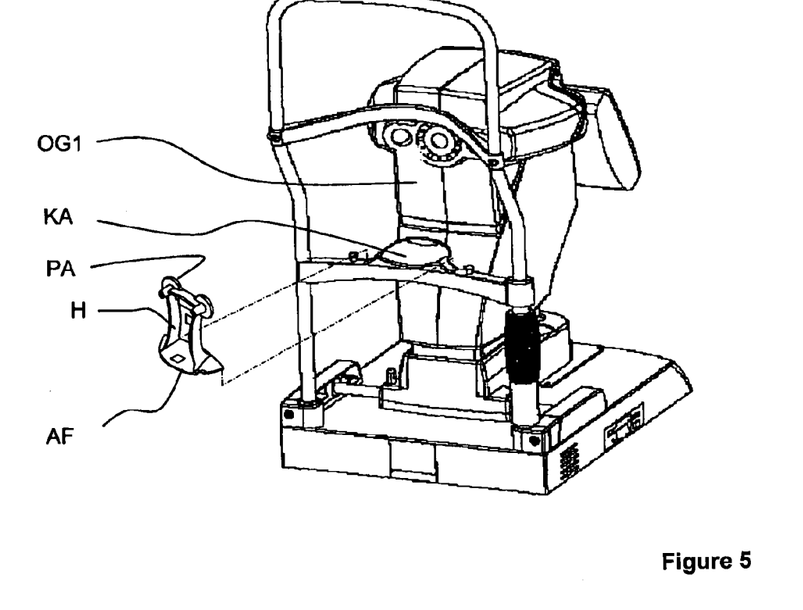
FIG. 5 depicts the test eyes in accordance with FIG. 4 in connection with an ophthalmological instrument based on interferometric measurement methods.

Hereto, FIG. 5 shows test eyes PA in accordance with FIG. 4 in connection with an ophthalmological instrument IOL based on an interferometric measurement method. As is indicated with the dotted line, the holder H with its seating surface AF is arranged on the chin rest KA of the ophthalmological instrument OG1, which is based on an interferometric measurement method.

Similar to the IOLMaster®, the calibration and test device, according to the invention, is, e.g., also suited for the calibration and/or adjustment of the so-called i.Profiler® from Carl Zeiss Meditec AG. The i.Profiler®, in contrast to the IOLMaster®, is based on the so-called wavefront technology and produces highly individual vision profiles of the eyes. The i.Profiler® is not only a keratometer and autorefractometer but also an additional aberrometer and a corneal topography system.

Figure 6:
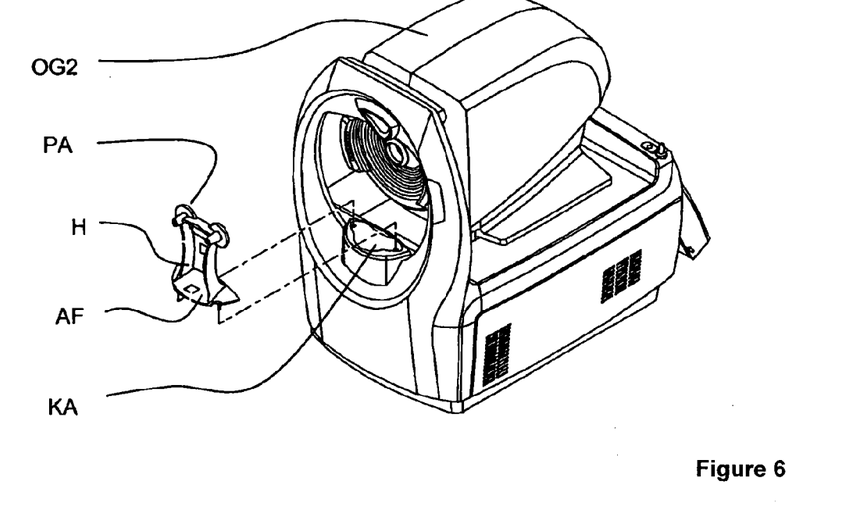
FIG. 6 depicts the test eyes in accordance with FIG. 4 in connection with an ophthalmological instrument based on the wavefront analysis.

Thereto, FIG. 6 shows test eyes PA in accordance with FIG. 4 in connection with an ophthalmological instrument OG2 based on the wavefront analysis. As is once again indicated with the dotted line, the holder H with its seating surface AF is arranged on the chin rest KA of the ophthalmological instrument OG2, which is based on the wavefront analysis.

With the use of the calibration and test device for the calibration and/or adjustment of ophthalmological measuring systems, it is particularly advantageous that not data of the calibration and test devices to be used have to be stored in the ophthalmological measuring system. The calibration as well as the adjustment of the ophthalmological measuring systems is effected exclusively by means of the individual physical data of the calibration and test device contained in the machine-readable identification. The only prerequisite is that the applied calibration and test devices are suited for the ophthalmological measuring system to be calibrated and/or adjusted.

In the method for the calibration and/or adjustment of ophthalmological measuring systems, according to the invention, the calibration and test device to be used is moved into the measuring position with the aid of at least one calibration and test device, its individual physical data are read by the ophthalmological measuring system to be calibrated and/or adjusted, its physical properties are measured by the ophthalmological measuring system to be calibrated and/or adjusted, the read physical data of the calibration and test device are compared with its measured physical properties, and findings about the state of calibration and/or adjustment as well a decision for the further utilization of the ophthalmological measuring system are derived. Thereto, a calibration and test device is used which exhibits a machine-readable identification, which contains its individual physical data.

For the calibration, a calibration and test device with barcode, data matrix code, RFID chip, or a similar electronic memory is put in the appropriate mount of the IOLMaster® by the operation personnel, and the measurement process is triggered. After the reading of the machine-readable identification of the calibration and test device, the measurement data are determined on the calibration and test device, and the results with regard to the machine-readable identification of the calibration and test device as well as the detected measurement errors are displayed to the operation personnel for the final decision. In a further step, said results can be documented, processed, used for adjustment, or also fed to an automatic utility assessment.

In a first preferred embodiment of the method, the individual physical data of the calibration and test device are hereby read and its physical properties measured with only one optical measurement device, i.e., with the optical imaging system already present in the ophthalmological measuring system to be calibrated and/or adjusted.

However, in principle it is also possible to use a separate optical measurement device, which is based on the optical imaging, for the reading of the individual physical data from the machine-readable identification of the calibration and test device. The measurement of the physical properties of the calibration and test device is effected with optical measurement devices, which are already present in the ophthalmological measuring system which is also based on the optical imaging.

In a second preferred embodiment of the method, the determined physical data as well as the measurements can be provided to the user, whereby this is preferably done in identical physical values. In addition, the user can also be presented with suggestions for tolerance positions and/or utility assessments in addition to the determined physical data and measurements of the calibration and test device.

However, it is hereby also possible that the utility assessment is processed fully automatically via a correct calibration and that, depending on the adjustment of the ophthalmological measuring system, said utility assessment leads to a disabling of the ophthalmological measuring system or only certain functions as well as additional measures.

Alternatively, it is of course also possible to automatically execute the alignment of the ophthalmological measuring system by means of the determined physical data and the measurements of the calibration and test device.

In a third preferred embodiment of the method, the ophthalmological measuring system to be calibrated and/or adjusted is put into the calibration and/or adjustment mode after the calibration and test device to be used was moved into the measuring position. Hereby, the cycles for the periodically required calibration and/or adjustment can be determined by the ophthalmological measuring system by means of the time elapsed or also the number of executed measurements, and displayed to the user.

Hereby, the switching of the ophthalmological measuring system to the calibration and/or adjustment mode upon detection of the machine-readable identification of the calibration and test device to be used can be effected automatically through the optical measurement device. Thereto, the calibration and test device must only be moved to the measuring position.

The solution, according to the invention, provides a calibration and test device for the calibration and/or adjustment of ophthalmological measuring systems which significantly simplifies the calibration and/or adjustment for the operation personnel.

Furthermore, the sources of error known from prior art, particularly a confusion or an incorrect decision due to lack of care, are ruled out.

As a result, the use of incorrect calibration and test devices and/or an incorrect assignment to the stored reference data is completely ruled out. The individual data of the calibration and test device are read from its machine-readable identification with every calibration and/or adjustment, so that incorrect measurements, which lead to misdiagnoses and even mistreatments, and calibration-related incorrect decisions are improbable.

With the suggested method, calibration and/or adjustment are very conveniently possible, so that the operation personnel no longer needs to dread said task which ultimately also serves to increase the safety of the device.

Moreover the solution, according to the invention, is a significant contribution to the effectiveness of the mandatory calibration, regardless of the level of qualification of the operation personnel, as well as to the trouble-free use of the technical instrument.

The invention claimed is:

1. An ophthalmological measuring system, for measurement of biometric data of an eye, comprising:
    an illumination source that illuminates an eye with light;
    a detection and analysis device that receives backscattered or reflected light portions;
    a control unit;
    at least one calibration and test device for verification of function and a state of calibration of a measuring system, integrated in the ophthalmological measuring system;
    the at least one calibration and test device including at least one test structure;
    wherein the test structure of the at least one calibration and test device includes a curved surface; and
    a device that incorporates the at least one calibration and test device into the ophthalmological measuring system and changes the position of the at least one calibration and test device between a calibration and test position in which the calibration and test device is presented with regard to the detection and analysis device that receives backscattered or reflected light portions and a storage position in which the calibration and test device is removed from the calibration and test position and stored integral to the ophthalmological measuring system; and
    wherein a device for attachment of the at least one calibration and test device includes structure with which the calibration and test device is moved mechanically and/or semi- or fully automatically between the calibration and test position and the storage position.

2. The ophthalmological measuring system, according to claim 1, further comprising structure that simultaneously illuminates the eye with light from different angles.

3. The ophthalmological measuring system, according to claim 2, wherein the structure that simultaneously illuminates the eye with light from different angles illuminates the eye at an angle greater than five degrees from the optical axis of the eye.

4. The ophthalmological measuring system, according to claim 1, wherein the device for the attachment and change of position of the calibration and test device with regard to the detection and analysis device further comprises means for movement of an additional optical element to align the calibration and test device with regard to the detection and analysis device that receives the backscattered or reflected light portions.

5. The ophthalmological measuring system, according to claim 1, wherein the at least one calibration and test device further comprises a device for attachment and wherein the device for attachment of the at least one calibration and test device includes an interface for identification of different calibration and test devices.

6. The ophthalmological measuring system, according to claim 1, wherein the ophthalmological measuring system further includes structure with which it is mechanically and/or semi- or fully automatically aligned with the calibration and test device.

7. The ophthalmological measuring system, according to claim 1, further comprising only one drive unit that mechanically and/or semi- or fully automatically aligns the calibration and test device with the ophthalmological measuring system and positions a headrest and/or chin rest.

8. The ophthalmological measuring system, according to claim 7, wherein said drive unit generates a linear movement for positioning of the headrest and/or chin rest, and generates a linear and/or rotating movement for alignment of the calibration and test device.

9. The ophthalmological measuring system, according to claim 1, wherein the calibration and test device is fixedly arranged and the ophthalmological measuring system further comprises structure deflecting the measuring beams of the ophthalmological measuring system to and/or into alignment with the fixedly arranged.

10. The ophthalmological measuring system, according to claim 5, wherein the device for attachment of the at least one calibration and test device is designed in such a way that the calibration and test device is exchangeable and can provide for various measuring tasks.

11. The ophthalmological measuring system, according to claim 5, wherein the device for attachment of the at least one calibration and test device is arranged directly on a headrest or a measuring head.

12. The ophthalmological measuring system, according to claim 5, wherein the device for attachment of the at least one calibration and test device further comprises a cover lid for the protection and/or means for the cleaning of the calibration and test device.

13. The ophthalmological measuring system, according to claim 1, further comprising safety devices which prevent a movement of the integrated calibration and test device when a head of a patient is situated on or near the headrest.

14. The ophthalmological measuring system, according to claim 5, further comprising means for detection of contamination of the calibration and test device.

15. The ophthalmological measuring system, according to claim 12, wherein the means for cleaning of the calibration and test device are based on mechanical, pneumatic, and/or acoustic methods.

16. The ophthalmological measuring system, according to claim 1, wherein the calibration and test device further comprises a machine-readable identification that contains individual physical data of the calibration and test device.

17. The ophthalmological measuring system, according to claim 16, wherein the machine-readable identification of the calibration and test device additionally contains tolerances required for calibration and/or adjustment of the ophthalmological measuring system, and/or information as to which calibration and test device is to be assigned to the ophthalmological measuring system.

18. The ophthalmological measuring system, according to claim 16, wherein the machine-readable identification of the calibration and test device comprises a barcode, a data matrix code, an RFID chip or an electronic memory.

19. The ophthalmological measuring system, according to claim 16, further comprising an appropriate device for activation and/or reading of the machine-readable identification.

20. The ophthalmological measuring system, according to claim 16, wherein the calibration and test device comprises a test eye with a barcode and wherein the calibration and the ophthalmological measuring system is based on an interferometric measuring method or wavefront analysis.

21. A method for the calibration and/or adjustment of an ophthalmological measuring system, comprising:
   moving a calibration and test device to be used to a measuring position from a storage position;
   reading individual physical data of the calibration and test device from a code structure incorporated physically into or onto the calibration and test device by a code reader operably coupled to the ophthalmological measuring system to be calibrated and/or adjusted;
   measuring physical properties of the calibration and test device by the ophthalmological measuring system to be calibrated and/or adjusted;
   comparing the read physical data of the calibration and test device with the measured physical properties;
   returning the calibration and test device to the storage position; and
   determining findings about a state of calibration and/or adjustment of the ophthalmological measuring system and deriving a decision about further utilization of the ophthalmological measuring system based thereon.

22. The method, according to claim 21, wherein the reading of the individual physical data of the calibration and test device and the measuring of the physical properties is effected with at least one optical measurement device which is based on optical imaging.

23. The method, according to claim 21, further comprising providing the user with the determined physical data and measurements in identical physical values.

24. The method, according to claim 23, further comprising presenting the user with suggestions for tolerance positions and/or utility assessments in addition to the determined physical data and measurements of the calibration and test device via the ophthalmological measuring system.

25. The method, according to claim 21, further comprising processing a utility assessment with regard to a correct calibration completely automatically and, depending on the adjustment of the ophthalmological measuring system, said utility assessment leads to a disabling of the ophthalmological measuring system or certain functions as well as additional measures.

26. The method, according to claim 21, further comprising executing alignment of the ophthalmological measuring system automatically based on the determined physical data and the measurements of the calibration and test device.

27. The method, according to claim 21, further comprising putting the ophthalmological measuring system to be calibrated and/or adjusted into a calibration and/or adjustment mode after the calibration and test device to be used is moved into the measuring position.

28. The method, according to claim 21, further comprising putting the ophthalmological measuring system to be calibrated and/or adjusted put into a calibration and/or adjustment mode automatically when the calibration and test device to be used is moved into the measuring position and machine-readable identification is detected by the optical measurement device.

* * * * *